(12) United States Patent
Lalleman et al.

(10) Patent No.: US 7,208,019 B2
(45) Date of Patent: Apr. 24, 2007

(54) TREATMENT OF DYED KERATIN FIBRES WITH A SURFACTANT COMPOSITION, AND USE FOR PROTECTING THE COLOR

(75) Inventors: Boris Lalleman, Paris (FR); Sylvain Kravtchenko, Asnieres (FR)

(73) Assignee: L'Oreal, Paris (FR)

( * ) Notice: Subject to any disclaimer, the term of this patent is extended or adjusted under 35 U.S.C. 154(b) by 316 days.

(21) Appl. No.: 11/004,817

(22) Filed: Dec. 7, 2004

(65) Prior Publication Data

US 2005/0144739 A1 Jul. 7, 2005

Related U.S. Application Data

(60) Provisional application No. 60/531,662, filed on Dec. 23, 2003.

(30) Foreign Application Priority Data

Dec. 11, 2003 (FR) .................... 03 14549

(51) Int. Cl.
*A61K 7/13* (2006.01)
(52) U.S. Cl. .................. 8/405; 8/407; 8/454; 8/455; 8/485; 8/636; 8/670; 8/677; 132/202; 132/208
(58) Field of Classification Search .................. 8/405, 8/407, 454, 455, 485, 636, 670, 677; 132/202, 132/208
See application file for complete search history.

(56) References Cited

U.S. PATENT DOCUMENTS

| 4,870,010 | A | 9/1989 | Hayes |
|---|---|---|---|
| 6,045,779 | A | 4/2000 | Mueller et al. |
| 6,432,146 | B1* | 8/2002 | Rondeau .................... 8/407 |
| 6,599,330 | B2 | 7/2003 | Tian et al. |
| 2001/0023514 | A1 | 9/2001 | Cottard et al. |
| 2003/0074747 | A1 | 4/2003 | Vuarier et al. |
| 2003/0150069 | A1 | 8/2003 | Kleen et al. |
| 2003/0229948 | A1 | 12/2003 | Desenne et al. |

FOREIGN PATENT DOCUMENTS

| JP | 9-508910 | 9/1997 |
|---|---|---|
| JP | 2000-212052 | 8/2000 |
| JP | 2001-206828 | 7/2001 |
| JP | 2001-294519 | 10/2001 |
| JP | 2002-249419 | 9/2002 |
| JP | 2003-55177 | 2/2003 |
| JP | 2003-192552 | 7/2003 |
| JP | 2003-535879 | 12/2003 |

OTHER PUBLICATIONS

K. Schrader: "Grundlagen und Rezepturen der Kosmetika", 1989, Huthig Buch Verlag, Heidelberg, XP002286009.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

Process for treating dyed human keratin fibres, in which the fibres are washed with a washing composition (B) containing at least one amphoteric surfactant and at least one nonionic surfactant chosen from alkylpolyglucosides and monoglycerolated or polyglycerolated surfactants. The invention also relates to a kit for performing this process.

41 Claims, No Drawings

TREATMENT OF DYED KERATIN FIBRES WITH A SURFACTANT COMPOSITION, AND USE FOR PROTECTING THE COLOR

REFERENCE TO PRIOR APPLICATIONS

This application claims priority to U.S. provisional application 60/531,662 filed Dec. 23, 2003, and to French patent application 0314549 filed Dec. 11, 2003, both incorporated herein by reference.

FIELD OF THE INVENTION

The present invention relates to a process for treating dyed keratin fibres, and also to the use of particular nonionic surfactants, or mixtures thereof, for protecting the coloration of the fibres.

More specifically, the field of the invention is that of the treatment of dyed keratin fibres, preferably human keratin fibres such as, especially, the hair.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

There are essentially two types of dyeing of keratin fibres: "permanent" dyeing and "semi-permanent" dyeing.

The first, also known as oxidation dyeing, uses "oxidation" dye precursors, which are colourless or weakly coloured compounds. Once mixed with oxidizing products, at the time of use, these precursors lead to coloured compounds and dyes via a process of oxidative condensation. In this case, the colorations obtained are generally very colour-fast and strong.

The second, also known as direct dyeing, uses direct dyes, which are nonionic or ionic dyes and coloured compounds capable of producing a more or less pronounced change of the natural colour of the hair, resistant to shampoo-washing several times. These dyes may or may not be used in the presence of an oxidizing agent.

In contrast with oxidation dye precursors, a direct dye is a relatively voluminous molecule that does not penetrate easily into the core of the fibre. Consequently, even though considerable progress has been made in this field, the phenomenon of bleeding of the coloration during shampooing is still non-negligible, even if the dye(s) used is (are) chosen from cationic species.

Moreover, the use of certain cationic direct dyes may be reflected by a reduction in the working qualities of the shampoos used after coloration, especially as regards the duration of the lather.

DETAILED DESCRIPTION OF THE PREFERRED EMBODIMENTS

One object of the present invention is, especially, to provide a process for treating dyed keratin fibres that can limit the phenomenon of bleeding of the colour during shampooing while at the same time benefiting from good working qualities for the shampoos.

Thus, one subject of the present invention is a process for treating human keratin fibres, in which the following steps are performed:

a) a step of dyeing the fibres is performed using a ready-to-use composition based on a dye composition comprising at least one cationic direct dye containing at least one heterocyclic group;

b) optionally, the fibres are washed with a washing composition (A) comprising at least one anionic detergent surfactant chosen from alkyl ether sulfates and/or alkyl sulfates, and the fibres are rinsed and optionally dried or left to dry;

c) the fibres are washed with a washing composition (B) comprising at least one nonionic surfactant chosen from alkylpolyglucosides and monoglycerolated or polyglycerolated surfactants, and mixtures thereof, and the fibres are then rinsed and dried or left to dry.

Step a) is not necessarily performed by the same person or at the same place performing steps b) and/or c), and is not necessarily performed at the same time as steps b) and/or c). In this regard the invention can be viewed as performing steps b) (which is optional) and c) on fibres that have been dyed using a ready-to-use composition based on a dye composition comprising at least one cationic direct dye containing at least one heterocyclic group. Such a process can be viewed as a process for treating human keratin fibres, comprising:

a) optionally washing fibres that have been dyed with a dye composition comprising at least one cationic direct dye, said cationic direct dye comprising at least one heterocyclic group, with a washing composition (A) comprising at least one anionic detergent surfactant selected from the group consisting of alkyl ether sulfates, alkyl sulfates, and mixtures thereof, rinsing said fibres, and optionally drying said fibres or leaving said fibres to dry;

b) washing said fibres that have been dyed with a dye composition comprising at least one cationic direct dye, said cationic direct dye comprising at least one heterocyclic group, with a washing composition (B) comprising at least one nonionic surfactant selected from the group consisting of alkylpolyglucosides, monoglycerolated surfactants, polyglycerolated surfactants, and mixtures thereof, and drying said fibres or leaving said fibres to dry.

A subject of the invention is similarly a kit for performing the invention process, comprising a dye composition and optionally a composition comprising at least one oxidizing agent; optionally at least one washing composition (A), and at least one washing composition (B). In one embodiment the dye composition is optional.

Another subject of the invention is a washing composition comprising, as surfactant, at least one nonionic surfactant chosen from alkylpolyglycosides and monoglycerolated or polyglycerolated surfactants, or mixtures thereof, for limiting the bleeding of the coloration and/or for protecting the coloration of keratin fibres, in relation with the prior use of a dye composition comprising at least one cationic direct dye comprising at least one heterocyclic group, and its use.

Specifically, it has been noted, surprisingly, that the use of a washing composition comprising at least one particular nonionic surfactant makes it possible to reduce the phenomenon of bleeding of the colour.

It has also been found, as a consequence, that the reduced bleeding of the dye(s) is reflected by a reduced risk of staining of the skin and fabrics.

Furthermore, the washing composition according to the invention has, entirely advantageously, very satisfactory working properties, for instance an abundance of lather that lasts for a long time.

Finally, the washing composition allows good protection of the coloration, which is reflected by reduced stripping-out of the coloration in the course of shampooing.

However, other advantages and characteristics of the invention will emerge more clearly on reading the description and the examples that follow.

As has been mentioned previously, in a preferred embodiment, the process according to the invention comprises, in a first step, in dyeing the fibres using a ready-to-use composition based on a dye composition comprising at least one cationic direct dye.

For the purposes of the invention, the term "cationic direct dye" means a dye bearing at least one quaternized nitrogen atom.

More particularly, the cationic direct dye(s) is (are) preferably chosen from xanthene dyes, azo dyes, azomethine dyes and methine dyes.

One or more dyes from those described in patent application EP 1 025 834 may in particular be used.

For example, the following compounds may conveniently be used:

$$G-N=N-J \qquad (I)$$

in which the symbol G represents a group chosen from the structures $G_1$ to $G_3$ below:

$G_1$ $G_2$ $G_3$ in which:

$R^1$ denotes a $C_1$–$C_4$ alkyl radical, a phenyl radical that may be substituted with a $C_1$–$C_4$ alkyl radical, or a halogen atom chosen from chlorine, bromine, iodine and fluorine;

$R_2$ denotes a $C_1$–$C_4$ alkyl radical or a phenyl radical;

$R_3$ and $R_4$, which may be identical or different, represent a $C_1$–$C_4$ alkyl radical, a phenyl radical, or form together in $G_1$ a benzene ring substituted with one or more $C_1$–$C_4$ alkyl, $C_1$–$C_4$ alkoxy or $NO_2$ radicals, or form together in $G_2$ a benzene ring optionally substituted with one or more $C_1$–$C_4$ alkyl, $C_1$–$C_4$ alkoxy or $NO_2$ radicals;

$R_3$ may also denote a hydrogen atom;

Z denotes an oxygen or sulfur atom or a group —$N^+R_7(X^-)$;

M represents a group —CH, —CR (R denoting $C_1$–$C_4$ alkyl) or —$N^+R_8(X^-)_r$;

K represents a group —CH, —CR (R denoting $C_1$–$C_4$ alkyl) or —$N^+R_8(X^-)_r$;

P represents a group —CH, —CR (R denoting $C_1$–$C_4$ alkyl) or —$N^+R_8(X^-)_r$;

M, K or P denoting a group —$N^+R_8(X^-)_r$;

r denotes 0 or 1;

$R_8$ represents an $O^-$ atom, a $C_1$–$C_4$ alkoxy radical or a $C_1$–$C_4$ alkyl radical;

$R_5$ and $R_6$, which may be identical or different, represent a hydrogen atom or a halogen atom chosen from chlorine, bromine, iodine and fluorine, a $C_1$–$C_4$ alkyl or $C_1$–$C_4$ alkoxy radical, or an —$NO_2$ radical;.

$X^-$ represents an anion preferably chosen from chloride, iodide, methyl sulfate, ethyl sulfate, acetate and perchlorate;

the symbol J represents:

(a) a group of structure $J_1$ below:

$J_1$ in which:

$R_9$ represents a hydrogen atom, a halogen atom chosen from chlorine, bromine, iodine and fluorine, a $C_1$–$C_4$ alkyl or $C_1$–$C_4$ alkoxy radical, an —OH, —$NO_2$, —$NHR_{12}$, —$NR_{13}R_{14}$ or $C_1$–$C_4$—NHCOalkyl radical, or forms with $R_{10}$ a 5- or 6-membered ring optionally containing one or more hetero atoms chosen from nitrogen, oxygen and sulfur;

$R_{10}$ represents a hydrogen atom, a halogen atom chosen from chlorine, bromine, iodine and fluorine, a $C_1$–$C_4$ alkyl or $C_1$–$C_4$ alkoxy radical, or forms with $R_{13}$ or $R_{14}$ a 5- or 6-membered ring optionally containing one or more hetero atoms chosen from nitrogen, oxygen and sulfur;

$R_{11}$ represents a hydrogen atom, an —OH radical, a radical —$NHR_{13}$ or a radical —$NR_{14}R_{15}$;

$R_{13}$ represents a hydrogen atom, a $C_1$–$C_4$ alkyl radical, a $C_1$–$C_4$ monohydroxyalkyl or $C_2$–$C_4$ polyhydroxyalkyl radical or a phenyl radical;

$R_{14}$ and $R_{15}$, which may be identical or different, represent a $C_1$–$C_4$ alkyl radical or a $C_1$–$C_4$ monohydroxyalkyl or $C_2$–$C_4$ polyhydroxyalkyl radical;

(b) a 5- or 6-membered nitrogenous heterocyclic group, which may contain other hetero atoms and/or carbonyl groups and may be substituted with one or more $C_1$–$C_4$ alkyl, amino or phenyl radicals, and especially a group of structure $J_2$ below:

$J_2$ in which:

$R_{16}$ and $R_{17}$, which may be identical or different, represent a hydrogen atom, a $C_{13}$–$C_{10}$ alkyl radical or a phenyl radical;

Y denotes a —CO— radical or a —C(CH$_3$)= radical;

n represents 0 or 1, with, when n denotes 1, U denoting a —CO— radical;

(II):

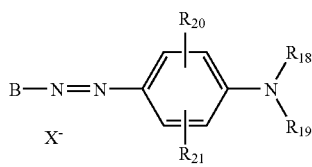

in which:

$R_{18}$ represents a hydrogen atom or a $C_1$–$C_4$ alkyl radical, $R_{19}$ represents a hydrogen atom, an alkyl radical possibly substituted with a —CN radical or with an amino group, a 4'-aminophenyl radical, or forms with $R_{18}$ a heterocycle optionally containing oxygen and/or nitrogen, possibly substituted with a $C_1$–$C_4$ alkyl radical, $R_{20}$ and $R_{21}$, which may be identical or different, represent a hydrogen atom, a halogen atom such as bromine, chlorine, iodine or fluorine, a $C_1$–$C_4$ alkyl or $C_1$–$C_4$ alkoxy radical, or a —CN radical, X$^-$ represents an anion preferably chosen from chloride, methyl sulfate and acetate, B represents a group chosen from structures B1 to B6 below:

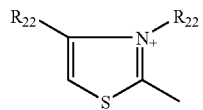
B1

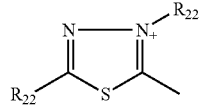
B2

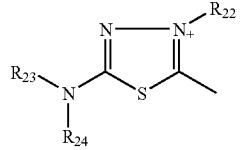
B3

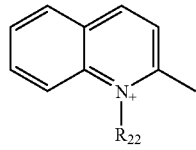
B4

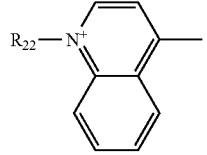
B5

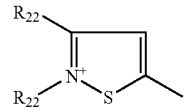
B6 in which $R_{22}$ represents a $C_1$–$C_4$ alkyl radical, $R_{23}$ and $R_{24}$, which may be identical or different, represent a hydrogen atom or a $C_1$–$C_4$ alkyl radical;

(III) and (IV):

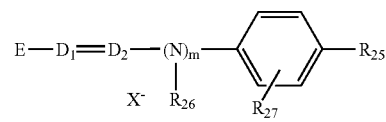
(III)

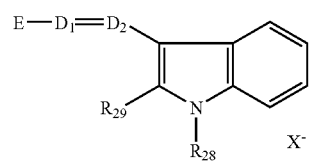
(IV)

in which:

$R_{25}$ represents a hydrogen atom, a $C_1$–$C_4$ alkoxy radical, a halogen atom such as bromine, chlorine, iodine or fluorine, or an amino radical, $R_{26}$ represents a hydrogen atom, a $C_1$–$C_4$ alkyl radical or forms, with a carbon atom of the benzene ring, a heterocycle optionally containing oxygen and/or substituted with one or more $C_1$–$C_4$ alkyl groups, $R_{27}$ represents a hydrogen atom or a halogen atom such as bromine, chlorine, iodine or fluorine, $R_{22}$ and $R_{23}$, which may be identical or different, represent a hydrogen atom or a $C_1$–$C_4$ alkyl radical, $D_1$ and $D_2$, which may be identical or different, represent a nitrogen atom or a —CH group, m represents 0 or 1, it being understood that when $R_{25}$ represents an unsubstituted amino group, then $D_1$ and $D_2$ simultaneously represent a —CH group and m=0, X$^-$ represents an anion preferably chosen from chloride, methyl sulfate and acetate, E represents a group chosen from structures E1 to E8 below:

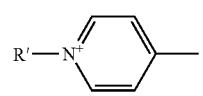
E1

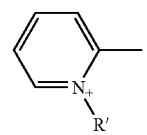
E2

-continued

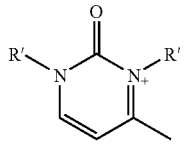
E3

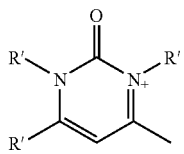
E4

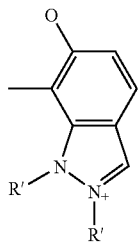
E5

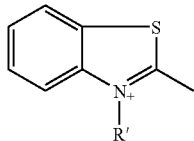
E6

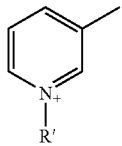
E7

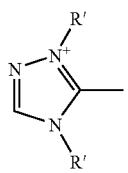
E8 in which R' represents a $C_1$–$C_4$ alkyl radical;

when m represents 0 and $D_1$ represents a nitrogen atom, then E may also denote a group of structure E9 below:

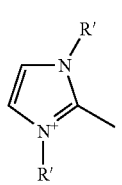
E9 in which R' represents a $C_1$–$C_4$ alkyl radical.

(V):

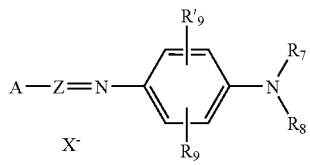
(V)

in which:

Z and D, which may be identical or different, represent a nitrogen atom or a —CH group, $R_7$ and $R_8$, which may be identical or different, represent a hydrogen atom; a $C_1$–$C_4$ alkyl radical possibly substituted with a —CN, —OH or —NH$_2$ radical, or form, with a carbon atom of the benzene ring, a heterocycle optionally containing oxygen or nitrogen, which may be substituted with one or more $C_1$–$C_4$ alkyl radicals; a 4'-aminophenyl radical, $R_9$ and $R'_9$, which may be identical or different, represent a hydrogen atom or a halogen atom chosen from chlorine, bromine, iodine and fluorine, or a cyano, $C_1$–$C_4$ alkyl, $C_1$–$C_4$ alkoxy or acetyloxy radical, $X^-$ represents an anion preferably chosen from chloride, methyl sulfate and acetate, A represents a group chosen from structures A1 to A18 below:

$A_1$ $A_2$ $A_3$ $A_4$ $A_5$

-continued

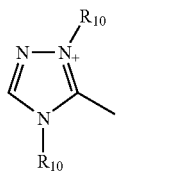 A6 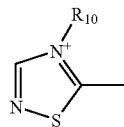

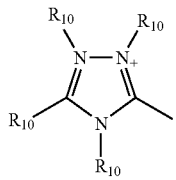 A7 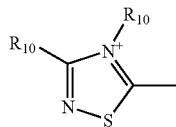

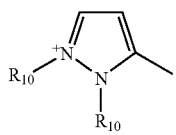 A8 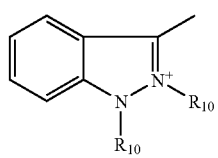

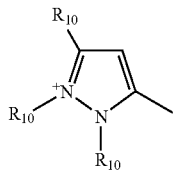

A9 in which $R_{10}$ represents a $C_1$–$C_4$ alkyl radical possibly substituted with a hydroxyl radical and $R_{11}$ represents a $C_1$–$C_4$ alkoxy radical.

The cationic dyes described in patent applications WO 95/01772, WO 95/15144, EP 714 954, EP 1 170 000, EP 1 166 753, EP 1 166 754 and EP 1 170 001, which are different from the above dyes, are similarly suitable for use. The passages in these patent applications concerning cationic dyes are incorporated into the present patent application.

A10

According to the invention, the cationic direct dye is chosen in particular from the following dyes:

cationic xanthene dyes, among which Acid Red 52 is preferably used, cationic azo or azomethine direct dyes, among which Basic Blue 41, Basic Blue 67, Basic Brown 1, Basic Brown 4, Basic Orange 31, Basic Red 18, Basic Red 22, Basic Red 46, Basic Red 51, Basic Red 104, Basic Violet 35, Basic Yellow 45, Basic Yellow 57, Basic Yellow 67 and Basic Yellow 87 may be used,

A11

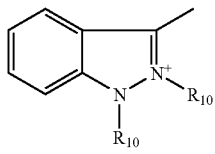

cationic methine direct dyes, such as, especially, Basic Red 14, Basic Yellow 13 and Basic Yellow 29.

A12

Heterocyclic cationic direct dyes bearing at least one cationic charge on a heterocycle are preferably used.

Azo dyes, methine dyes or azomethine dyes bearing at least one cationic charge on a heterocycle are most particularly used.

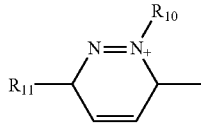

The cationic direct dye(s) used in the dye composition advantageously represent(s) from 0.0001% to 20% by weight, more particularly from 0.001% to 10% by weight and preferably from 0.01% to 5% by weight relative to the total weight of the dye composition.

A13

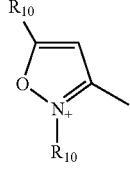

It should be noted that the dye composition may optionally comprise other types of direct dyes, for instance nonionic direct dyes.

A14

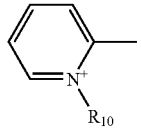

If this type of dye is present, its content may generally represents less than 5% by weight relative to the weight of the dye composition.

A15

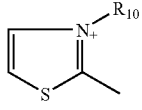

In accordance with another embodiment of the invention, the dye composition comprises at least one oxidation base and optionally at least one coupler.

The compounds of this type conventionally used in the field of dyeing keratin fibres, especially human keratin fibres, may be used in the dye composition.

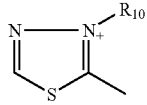

Thus, the oxidation bases can be chosen, in particular, from para-phenylenediamines, double bases, para-aminophenols, ortho-aminophenols and heterocyclic oxidation bases.

Among the para-phenylenediamines that may be used as oxidation bases in the dye compositions in accordance with the invention, mention may be made in particular of the compounds of formula (I) below, and the addition salts thereof with an acid:

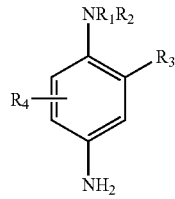

(I)

in which:
$R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical, a $C_1$–$C_4$ alkyl radical substituted with a nitrogenous group, a phenyl radical or a 4'-aminophenyl radical;
$R_2$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous group;
$R_3$ represents a hydrogen atom, a halogen atom such as a chlorine, bromine, iodine or fluorine atom, a $C_1$–$C_4$ alkyl radical, a $C_1$–$C_4$ monohydroxyalkyl radical, a $C_1$–$C_4$ hydroxyalkoxy radical, an acetylamino$(C_1$–$C_4)$alkoxy radical, a $C_1$–$C_4$ mesylaminoalkoxy radical or a carbamoylamino$(C_1$–$C_4)$alkoxy radical,
$R_4$ represents a hydrogen or halogen atom or a $C_1$–$C_4$ alkyl radical.

Among the para-phenylenediamines of formula (I) above, mention may be made more particularly of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-□-hydroxyethyloxy-para-phenylenediamine, 2-β-acetylaminoethyloxy-para-phenylenediamine and N-(β-methoxyethyl)-para-phenylenediamine, and the addition salts thereof with an acid.

According to the invention, the term "double bases" is understood to refer to the compounds containing at least two aromatic rings bearing amino and/or hydroxyl groups.

Among the double bases that may be used as oxidation bases in the dye compositions in accordance with the invention, mention may be made in particular of the compounds corresponding to formula (II) below, and the addition salts thereof with an acid:

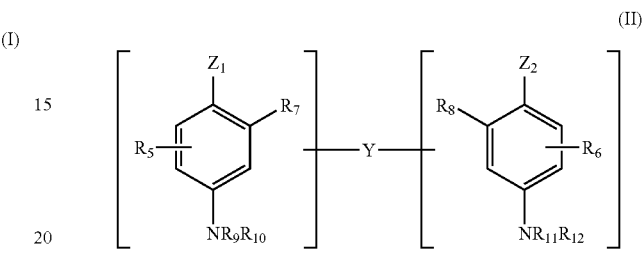

(II)

in which:
$Z_1$ and $Z_2$, which may be identical or different, represent a hydroxyl or —$NH_2$ radical possibly substituted with a $C_1$–$C_4$ alkyl radical or with a linker arm Y;
the linker arm Y represents a linear or branched alkylene chain containing from 1 to 14 carbon atoms, which may be interrupted by or terminated with one or more nitrogenous groups and/or one or more hetero atoms such as oxygen, sulfur or nitrogen atoms, and optionally substituted with one or more hydroxyl or $C_1$–$C_6$ alkoxy radicals;
$R_5$ and $R_6$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;
$R_7$, $R_8$, $R_9$, $R_{10}$, $R_{11}$ and $R_{12}$, which may be identical or different, represent a hydrogen atom, a linker arm Y or a $C_1$–$C_4$ alkyl radical;
it being understood that the compounds of formula (II) contain only one linker arm Y per molecule.

Among the nitrogenous groups of formula (II) above, mention may be made in particular of amino, mono$(C_1$–$C_4)$alkylamino, di$(C_1$–$C_4)$alkylamino, tri$(C_1$–$C_4)$alkylamino, monohydroxy$(C_1$–$C_4)$alkylamino, imidazolinium and ammonium radicals.

Among the double bases of formula (II) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-amino-phenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among the para-aminophenols that may be used as oxidation bases in the dye compositions in accordance with the invention, mention may be made in particular of the compounds corresponding to formula (III) below, and the addition salts thereof with an acid:

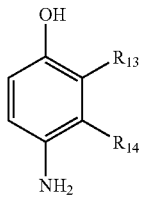

(III)

in which:
R$_{13}$ represents a hydrogen or halogen atom or a C$_1$–C$_4$ alkyl, C$_1$–C$_4$ monohydroxyalkyl, (C$_1$–C$_4$)alkoxy(C$_1$–C$_4$)alkyl, C$_1$–C$_4$ aminoalkyl or hydroxy(C$_1$–C$_4$)alkylamino(C$_1$–C$_4$) alkyl radical, R$_{14}$ represents a hydrogen or halogen atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy-(C$_1$–C$_4$)alkyl radical, it being understood that at least one of the radicals R$_{13}$ or R$_{14}$ represents a hydrogen atom.

para-Aminophenols that may also be mentioned include 4-amino-6-[(5'-amino-2'-hydroxy-3'-methylphenyl)methyl]-2-methylphenol and bis(5-amino-2'-hydroxyphenyl)methane, and the addition salts thereof with an acid.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methyl-phenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be used as oxidation bases in the dye compositions in accordance with the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases that may be used as oxidation bases in the dye compositions in accordance with the invention, mention may be made more particularly of pyridine derivatives, pyrimidine derivatives, pyrazole derivatives and pyrazolopyrimidine derivatives, and the addition salts thereof with an acid.

Among the pyridine derivatives, mention may be made more particularly of the compounds described, for example, in patents GB 1,026,978 and GB 1,153,196, such as 2,5-diaminopyridine, 2-(4-methoxyphenyl)amino-3-amino-pyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2,359,399 or Japanese patents JP 88-169,571 and JP 91-333 495 or patent applications WO 96/15765, such as 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof with an acid.

Among the pyrazole derivatives, mention may be made more particularly of the compounds described in patents DE 3,843,892, DE 4,133,957 and patent applications WO 94/08969, WO 94/08970, FR-A-2,733,749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

Among the pyrazolopyrimidine derivatives, mention may be made more particularly of the pyrazolo[1,5-a]pyrimidines of formula (IV) below, and the addition salts thereof with an acid or with a base and the tautomeric forms thereof, when a tautomeric equilibrium exists:

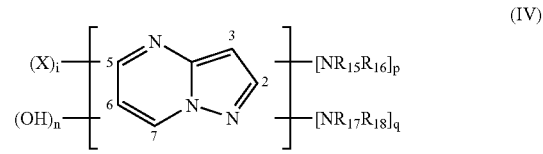

(IV)

in which:
R$_{15}$, R$_{16}$, R$_{17}$ and R$_{18}$, which may be identical or different, denote a hydrogen atom, a C$_1$–C$_4$ alkyl radical, an aryl radial, a C$_1$–C$_4$ hydroxyalkyl radical, a C$_2$–C$_4$ polyhydroxyalkyl radical, a (C$_1$–C$_4$)alkoxy(C$_1$–C$_4$)alkyl radical, a C$_1$–C$_4$ aminoalkyl radical (it being possible for the amine to be protected with an acetyl, ureido or sulfonyl radical), a (C$_1$–C$_4$)alkylamino(C$_1$–C$_4$)alkyl radical, a di[(C$_1$–C$_4$)alkyl]amino(C$_1$–C$_4$)alkyl radical (it being possible for the dialkyl radicals to form a 5- or 6-membered carbon-based ring or a heterocycle), a hydroxy(C$_1$–C$_4$)alkyl- or di[hydroxy(C$_1$–C$_4$)alkyl]amino(C$_1$–C$_4$)alkyl radical;

the radicals X, which may be identical or different, denote a hydrogen atom, a C$_1$–C$_4$ alkyl radical, an aryl radical, a C$_1$–C$_4$ hydroxyalkyl radical, a C$_2$–C$_4$ polyhydroxyalkyl radical, a C$_1$–C$_4$ aminoalkyl radical, a (C$_1$–C$_4$)alkylamino(C$_1$–C$_4$)alkyl radical, a di[(C$_1$–C$_4$)alkyl]amino(C$_1$–C$_4$) alkyl radical (it being possible for the dialkyls to form a 5- or 6-membered carbon-based ring or a heterocycle), a hydroxy(C$_1$–C$_4$)alkyl- or di-[hydroxy(C$_1$–C$_4$)alkyl]amino(C$_1$–C$_4$)alkyl radical, an amino radical, a (C$_1$–C$_4$) alkyl- or di[(C$_1$–C$_4$)alkyl]amino radical; a halogen atom, a carboxylic acid group, a sulfonic acid group;

i is equal to 0, 1, 2 or 3; p is equal to 0 or 1; q is equal to 0 or 1; n is equal to 0 or 1; with the proviso that the sum p+q is other than 0;

when p+q is equal to 2, then n is equal to 0 and the groups NR$_{15}$R$_{16}$ and NR$_{17}$R$_{18}$ occupy the (2,3); (5,6); (6,7); (3,5) or (3,7) positions;

when p+q is equal to 1, then n is equal to 1 and the group $NR_{15}R_{16}$ (or $NR_{17}R_{18}$) and the OH group occupy the (2,3); (5,6); (6,7); (3,5) or (3,7) positions.

Among the pyrazolo[1,5-a]pyrimidines of formula (IV) above, mention may be made in particular of pyrazolo[1,5-a]pyrimidine-3,7-diamine; 2,5-dimethyl-pyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)-(2-hydroxyethyl)-amino]ethanol; 2-[(7-aminopyrazolo[1,5-a]pyrimidin-3-yl)-(2-hydroxy-ethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetra-methylpyrazolo[1,5-a]pyrimidine-3,7-diamine; and the addition salts thereof and the tautomeric forms thereof, when a tautomeric equilibrium exists.

When the dye composition comprises one or more oxidation bases, their content usually represents from 0.0005% to 12% by weight and preferably from 0.005% to 8% by weight relative to the total weight of the dye composition.

The dye composition may also comprise at least one coupler associated with one or more oxidation bases.

These couplers are advantageously chosen from those conventionally used in oxidation dye compositions, i.e. meta-phenylenediamines, meta-aminophenols, meta-diphenols and heterocyclic couplers, and the addition salts thereof with an acid.

These couplers can be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the addition salts thereof with an acid.

When they are present in the dye composition, the coupler content generally represents from 0.0001% to 10% by weight and preferably from 0.005% to 5% by weight relative to the weight of the dye composition.

In general, the addition salts with an acid that may be used in the context of the dye compositions of the invention (oxidation bases and couplers) are chosen in particular from the hydrochlorides, hydrobromides, sulfates, tartrates, lactates and acetates.

It should be noted that the dye composition used during this first step may comprise any additive that is common in this type of composition. Thus, it may comprise additives such as anionic, cationic, nonionic, amphoteric or zwitterionic surfactants or mixtures thereof; polymers; thickeners; antioxidants; penetrating agents; sequestering agents; fragrances; dispersants; film-forming agents; UV-screening agents; vitamins; preserving agents; opacifiers, especially [lacuna].

The adjuvants mentioned above are generally present in an amount, for each of them, of between 0.01% and 20% by weight relative to the weight of the composition.

Finally, the dye composition comprises a medium that is suitable for keratin fibres, which may generally comprise water or of a mixture of water and of at least one cosmetically acceptable organic solvent, to dissolve the compounds that are not sufficiently water-soluble.

Examples of organic solvents that may be mentioned include linear or branched, preferably saturated, monoalcohols containing from 2 to 10 carbon atoms, such as ethyl alcohol or isopropyl alcohol; aromatic alcohols such as benzyl alcohol or phenylethyl alcohol; polyols or polyol ethers, for instance ethylene glycol monomethyl ether, monoethyl ether and monobutyl ether, propylene glycol or ethers thereof, for instance propylene glycol monomethyl ether, butylene glycol, dipropylene glycol, hexylene glycol (2-methyl-2,4-pentanediol), neopentyl glycol and 3-methyl-1,5-pentanediol; and also diethylene glycol alkyl ethers, especially of $C_1$–$C_4$, for instance diethylene glycol monoethyl ether or monobutyl ether, alone or as a mixture.

The solvents may be present in proportions preferably of between 1% and 40% by weight approximately and even more preferably between 5% and 30% by weight approximately, relative to the total weight of the dye composition.

Usually, the pH of the dye compositions ranges between 4 and 12 and preferably between 6 and 11.

According to a first embodiment, the ready-to-use composition applied to the keratin fibres does not comprise an oxidizing agent. In this case, the ready-to-use composition corresponds to the dye composition.

This embodiment is particularly suitable when the composition does not comprise any oxidation base(s) or coupler(s).

According to a second embodiment, the ready-to-use composition is applied to the keratin fibres in the presence of an oxidizing agent.

This embodiment is suitable irrespective of the nature of the dyes present in the dye composition.

Conventionally, the oxidizing agent is chosen especially from hydrogen peroxide, urea peroxide, alkali metal bromates or ferricyanides, persalts, redox enzymes such as laccases, peroxidases and 2-electron oxidoreductases, where appropriate in the presence of the respective donor thereof.

In the case of this second embodiment, the ready-to-use composition is obtained by mixing, before application to the fibres, a dye composition as described above with a composition comprising at least one oxidizing agent.

According to this process, at least one ready-to-use composition is applied to the fibres for a time that is sufficient to develop the desired coloration, after which the fibres are optionally rinsed.

The time required to develop the coloration is generally between 1 and 60 minutes and even more precisely between 5 and 40 minutes.

The temperature at which this step is performed generally ranges between 20° C. and 80° C.

Once the dyeing step a) has been performed, optionally followed by rinsing, the keratin fibres are optionally washed using a washing composition (A) comprising at least one anionic detergent surfactant chosen from alkyl ether sulfates and/or alkyl sulfates, after which the fibres are rinsed and optionally dried or left to dry.

It should be noted that the alkyl portions of the alkyl ether sulfates and/or alkyl sulfates listed above advantageously contain from 6 to 24 carbon atoms and more particularly from 8 to 18 carbon atoms.

Usually, the content of anionic detergent surfactant in this composition is between 4% and 50% by weight relative to the weight of the washing composition (A), and preferably from 6% to 30% by weight relative to the weight of the washing composition (A).

The washing composition (A) may also comprise one or more nonionic, amphoteric or zwitterionic, or mild anionic surfactants.

More particularly, nonionic surfactants that may be mentioned include:
oxyalkylenated or polyglycerolated fatty alcohols;
oxyalkylenated alkylphenols, the alkyl chain of which is of $C_8$–$C_{18}$;
oxyalkylenated or polyglycerolated fatty amides;
oxyalkylenated fatty amines;
oxyalkylenated plant oils;
optionally oxyalkylenated fatty acid esters of sorbitan;
optionally oxyalkylenated fatty acid esters of sucrose;
fatty acid esters of polyethylene glycol;
alkylpolyglycosides;
N-alkylglucamine derivatives;
amine oxides such as ($C_{10}$–$C_{14}$)alkylamine oxides or N-acylaminopropylmorpholine oxides;
copolymers of ethylene oxide and of propylene oxide.

The term "fatty chain" means a linear or branched, saturated or unsaturated hydrocarbon-based chain containing from 6 to 30 carbon atoms and preferably from 8 to 24 carbon atoms.

More particularly, the mean number of oxyalkylene units is between 2 and 30 units. They are preferably oxyethylene or oxypropylene units, or mixtures thereof.

As regards the polyglycerolated surfactants, they preferably comprise on average 1 to 5 and in particular 1.5 to 4 glycerol groups.

As regards the amphoteric or zwitterionic surfactants, mention may be made, without wishing to be limited thereto, of aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); mention may also be made of ($C_8$–$C_{20}$)alkylbetaines, sulfobetaines, ($C_8$–$C_{20}$)alkylamido($C_1$–$C_6$)alkylbetaines or ($C_8$–$C_{20}$)alkylamido($C_1$–$C_6$)alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

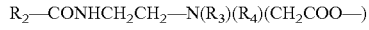
$R_2$—CONHCH$_2$CH$_2$—N(R$_3$)(R$_4$)(CH$_2$COO—)

in which:
$R_2$ denotes an alkyl radical of an acid $R_2$—COOH present in hydrolysed coconut oil,
a heptyl, nonyl or undecyl radical,
$R_3$ denotes a beta-hydroxyethyl group and
$R_4$ denotes a carboxymethyl group; and

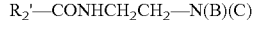
$R_2'$—CONHCH$_2$CH$_2$—N(B)(C)

in which:
B represents —CH$_2$CH$_2$OX', C represents —(CH$_2$)$_z$—Y', with z=1 or 2,
X' denotes the —CH$_2$CH$_2$—COOH group or a hydrogen atom,
Y' denotes —COOH or the —CH$_2$—CHOH—SO$_3$H radical, $R_{2'}$ denotes an alkyl radical of an acid $R_9$—COOH present in coconut oil or in hydrolysed linseed oil, an alkyl radical, in particular a $C_7$, $C_9$, $C_{11}$ or $C_{13}$ alkyl radical, a $C_{17}$ alkyl radical and its iso form, or an unsaturated $C_{17}$ radical.

These compounds are classified in the CTFA dictionary, 5th edition, 1993, under the names disodium cocoamphodiacetate, disodium lauroamphodiacetate, disodium caproamphodiacetate, disodium capryloampho-diacetate, disodium cocoamphodipropionate, disodium lauroamphodipropionate, disodium caproamphodipropionate, disodium capryloamphodipropionate, lauro-amphodipropionic acid, cocoamphodipropionic acid and disodium cocoamphocarboxyethyl hydroxypropyl sulfonate. By way of example, mention may be made of the cocoamphodiacetate sold under the trade name Miranol® C2M Concentrate by the company Rhodia Chimie.

Mention may also be made of the derivatives of formula RCONH(CH$_2$)$_n$N(Y$_2$—X$_1$)(Y$_1$—X$_2$), in which formula:
$Y_2$ and $Y_1$ are divalent radicals, which may be identical or different, chosen from linear or branched $C_1$–$C_6$ alkylene radicals optionally substituted with one or more hydroxyl radicals,
$X_1$ and $X_2$, which may be identical or different, are $C_1$–$C_6$ hydrocarbon-based radicals optionally interrupted with one or more hetero atoms and bearing at least one acid salt function chosen from carboxylate, sulfonate, sulfate, phosphate and phosphonate groups,
n denotes an integer ranging from 1 to 6.

As regards the mild anionic surfactants, mention may be made especially of the compounds having the following formulae, and also mixtures thereof:
polyoxyalkylenated alkyl ether carboxylic acids;
polyoxyalkylenated alkylaryl ether carboxylic acids;
polyoxyalkylenated alkylamido ether carboxylic acids, in particular those comprising from 2 to 50 ethylene oxide groups;
alkyl-D-galactosiduronic acids;
acylsarcosinates and acylglutamates;
alkylpolyglycoside carboxylic esters;
fatty acid salts.

Polyoxyalkylenated alkyl ether carboxylic acids, for instance lauryl ether carboxylic acid (4.5 OE) sold, for example, under the name Akypo RLM 45 CA from Kao, are most particularly used.

When they are present, the content of mild anionic, amphoteric and/or zwitterionic surfactants represents from 4% to 50% by weight relative to the total weight of the surfactants present in the first washing composition (A).

The washing composition (A) may also comprise additives, for instance those chosen from the non-exhaustive list such as reducing agents, antioxidants, sequestering agents, softeners, antifoams, moisturizers, emollients, basifying agents, plasticizers, sunscreens, direct dyes or oxidation dyes, pigments, mineral fillers, clays, colloidal minerals, nacres, nacreous agents, fragrances, peptizers, preserving agents, fixing or non-fixing polymers, proteins, vitamins, antidandruff agents, aliphatic or aromatic alcohols, and more particularly ethanol, benzyl alcohol, modified or unmodified polyols, such as glycerol, glycol, propylene glycol, dipropylene glycol, butylene glycol or butyl diglycol, volatile silicones, mineral, organic or plant oils, oxyethylenated or non-oxyethylenated waxes, paraffins, fatty acids, associative or non-associative thickening polymers, fatty amides, fatty esters, fatty alcohols, etc.

The adjuvants mentioned above are generally preferably present in an amount, for each of them, of between 0.01% and 20% by weight relative to the weight of the composition.

It should be noted that if the composition comprises one or more thickeners, their content is preferably between 0.01% and 20% by weight relative to the weight of the washing composition, and more preferably from 0.01% to 3% by weight relative to the weight of the washing composition.

The composition according to the invention may contain a propellant. The propellant consists of the compressed or liquefied gases usually used for the preparation of aerosol compositions. Air, carbon dioxide, compressed nitrogen, or a soluble gas such as dimethyl ether, halohydrocarbons (in particular fluorohydrocarbons) or non-halo hydrocarbons, and mixtures thereof, will preferably be used.

The compositions may be in any form, including any of the various galenical forms, such as a lotion, a spray, an aerosol mousse, a pump mousse, etc.

Preferably, the washing composition (A) comprises at least one conditioning agent, which is preferably cationic.

According to this embodiment, the content of conditioning agent in the washing composition (A) is preferably between 0.01% and 20% by weight relative to the weight of the washing composition (A).

According to one preferred embodiment, the conditioning agent is a cationic polymer and/or a volatile or non-volatile silicone, preferably an amino silicone.

For the purpose of the present invention, the term "cationic polymer" denotes any polymer containing cationic groups and/or groups that may be ionized into cationic groups.

The cationic polymers that may be used in accordance with the present invention may be chosen from all those already known per se as improving the cosmetic properties of hair treated with detergent compositions, i.e. especially those described in patent application EP-337 354 and in French patent applications FR-2 270 846, 2 383 660, 2 598 611, 2 470 596 and 2 519 863.

The cationic polymers that are preferred are chosen from those containing units comprising primary, secondary, tertiary and/or quaternary amine groups that may either form part of the main polymer chain or be borne by a side substituent directly attached thereto.

The cationic polymers used generally have a number-average molecular mass of between 500 and $5 \times 10^6$ approximately and preferably between $10^3$ and $3 \times 10^6$ approximately.

Among the cationic polymers that may be mentioned more particularly are polymers of the polyamine, polyamino amide and polyquaternary ammonium type.

The polymers of the polyamine, polyamino amide and polyquaternary ammonium type that may be used in accordance with the present invention, and that may especially be mentioned, are those described in French patents Nos 2 505 348 and 2 542 997. Among these polymers, particular mention may be made of:

(1) homopolymers or copolymers derived from acrylic or methacrylic esters or amides and comprising at least one of the units of the following formulae:

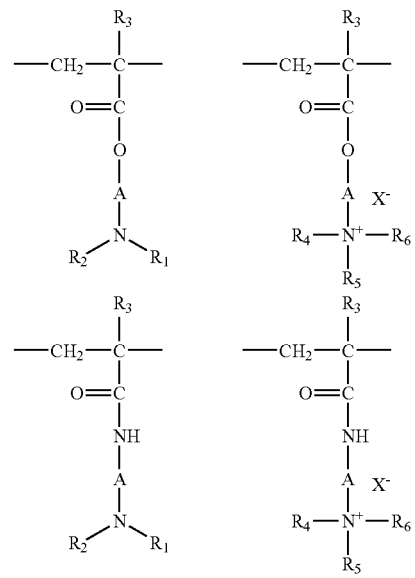

in which:
$R_3$, which may be identical or different, denote a hydrogen atom or a $CH_3$ radical;
A, which may be identical or different, represent a linear or branched alkyl group of 1 to 6 carbon atoms, preferably 2 or 3 carbon atoms, or a hydroxyalkyl group of 1 to 4 carbon atoms;
$R_4$, $R_5$, $R_6$, which may be identical or different, represent an alkyl group containing from 1 to 18 carbon atoms or a benzyl radical and preferably an alkyl group containing from 1 to 6 carbon atoms;
$R_1$ and $R_2$, which may be identical or different, represent hydrogen or an alkyl group containing from 1 to 6 carbon atoms, and preferably methyl or ethyl;
X denotes an anion derived from a mineral or organic acid, such as a methosulfate anion or a halide such as chloride or bromide.

The copolymers of family (1) can also contain one or more units derived from comonomers that may be chosen from the family of acrylamides, methacrylamides, diacetone acrylamides, acrylamides and methacrylamides substituted on the nitrogen with lower ($C_1$–$C_4$) alkyls, acrylic or methacrylic acids or esters thereof, vinyllactams such as vinylpyrrolidone or vinylcaprolactam, and vinyl esters.

Thus, among these copolymers of family (1), mention may be made of:
copolymers of acrylamide and of dimethylaminoethyl methacrylate quaternized with dimethyl sulfate or with a dimethyl halide, such as the product sold under the name Hercofloc® by the company Hercules,
the copolymers of acrylamide and of methacryloyloxyethyltrimethylammonium chloride described, for example, in patent application EP-A-080 976 and sold under the name Bina Quat P 100® by the company Ciba Geigy,
the copolymer of acrylamide and of methacryloyloxyethyltrimethylammonium methosulfate sold under the name Reten® by the company Hercules,
quaternized or nonquaternized vinylpyrrolidone/dialkylaminoalkyl acrylate or methacrylate copolymers, such as the products sold under the name "Gafquat" by the company ISP, such as, for example, "Gafquat 734" or "Gafquat 755", or alternatively the products known as "Copolymer 845, 958 and 937". These polymers are described in detail in French patents 2 077 143 and 2 393 573, dimethylaminoethyl methacrylate/vinylcaprolactam/vinylpyrrolidone terpolymers, such as the product sold under the name Gaffix® VC 713 by the company ISP, vinylpyrrolidone/methacrylamidopropyldimethylamine copolymers sold in particular under the name Styleze® CC 10 by ISP, and quaternized vinylpyrrolidone/dimethylaminopropylmethacrylamide copolymers, such as the product sold under the name "Gafquat® HS 100" by the company ISP.

(2) The cellulose ether derivatives containing quaternary ammonium groups, described in French patent 1 492 597, and in particular polymers sold under the names "JR" (JR 400, JR 125 and JR 30M) or "LR" (LR 400 or LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers or cellulose derivatives grafted with a water-soluble quaternary ammonium monomer, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial products corresponding to this definition are more particularly the products sold under the names "Celquat® L 200" and "Celquat® H 100" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar® C13 S, Jaguar® C15, Jaguar® C 17 and Jaguar® C 162 by the company Rhodia Chimie.

(5) polymers consisting of piperazinyl units and of divalent alkylene or hydroxyalkylene radicals containing straight or branched chains, optionally interrupted by oxygen, sulfur or nitrogen atoms or by aromatic or heterocyclic rings, as well as the oxidation and/or quaternization products of these polymers. Such polymers are described, in particular, in French patents 2 162 025 and 2 280 361;

(6) water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound that is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508;

(7) the polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylaminohydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (Va) or (Vb):

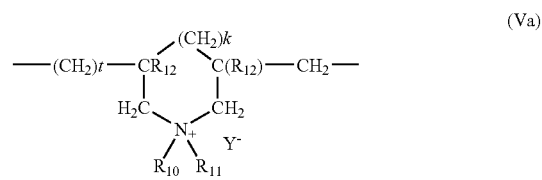

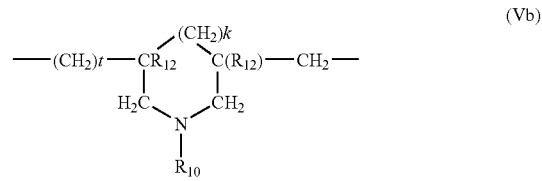

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group having from 1 to 22 carbon atoms, a hydroxyalkyl group in which the alkyl group preferably has 1 to 5 carbon atoms, a lower ($C_1$–$C_4$) amidoalkyl group, or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

$R_{10}$ and $R_{11}$, independently of each other, preferably denote an alkyl group containing from 1 to 4 carbon atoms.

Among the polymers defined above, mention may be made more particularly of the dimethyldiallylammonium chloride homopolymer sold under the name "Merquat® 100" by the company Nalco (and its homologs of low weight-average molecular mass) and the copolymers of diallyldimethylammonium chloride and of acrylamide, sold under the name "Merquat®550".

(10) The quaternary diammonium polymer containing repeating units corresponding to formula (VI):

in which formula (VI):

$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second hetero atom other than nitrogen, or alternatively $R_{13}$, $R_{14}$, $R_{15}$ and $R_{16}$ represent a linear or branched $C_1$–$C_6$ alkyl radical substituted with a nitrile, ester, acyl or amide group or a group —CO—O—$R_{17}$-D or —CO—NH—$R_{17}$-D where $R_{17}$ is an alkylene and D is a quaternary ammonium group;

$A_1$ and $B_1$ represent polymethylene groups containing from 2 to 20 carbon atoms, which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid, preferably $Cl^-$ or $Br^-$;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group $(CH_2)_n$—CO-D-OC—$(CH_2)_n$— in which D denotes: a) a glycol residue of formula: —O-Z-O—, where Z denotes a linear or branched hydrocarbon-based radical or a group corresponding to one of the following formulae: —$(CH_2$—$CH_2$—O)x-$CH_2$—$CH_2$—/— [$CH_2$—$CH(CH_3)$—O]$_y$—$CH_2$—$CH(CH_3)$— where x and y denote an integer from 1 to 4, representing a defined and unique degree of polymerization or any number from 1 to 4 representing an average degree of polymerization; b) a bis-secondary diamine residue such as a piperazine derivative; c) a bis-primary diamine residue of formula: —NH—Y—NH—, where Y denotes a linear or branched hydrocarbon-based radical, or alternatively the divalent radical —$CH_2$—$CH_2$—S—S—$CH_2$—$CH_2$—; d) a ureylene group of formula: —NH—CO—NH—; n ranges from 1 to 6.

These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the formula:

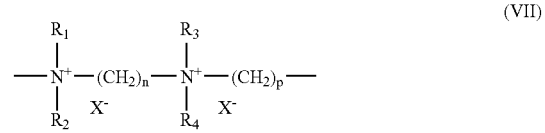

in which $R_1$, $R_2$, $R_3$ and $R_4$, which may be identical or different, denote an alkyl or hydroxyalkyl radical containing from 1 to 4 carbon atoms approximately, n and p are integers ranging from 2 to 20 approximately, and $X^-$ is an anion derived from a mineral or organic acid.

A compound of formula (VII) that is particularly preferred is the compound for which $R_1$, $R_2$, $R_3$ and $R_4$ represent a methyl radical and n=3, p=6 and X=Cl, referred to as hexadimethrine chloride according to the INCI nomenclature (CTFA).

(11) Polyquaternary ammonium polymers consisting of units of formula (VIII):

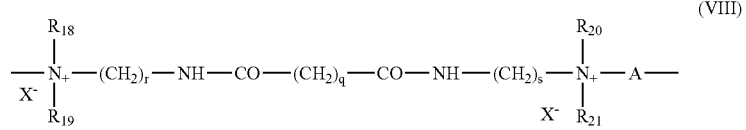

in which formula:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2$ $(OCH_2CH_2)_p$OH radical, where p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers ranging from 1 to 6, q is equal to 0 or to an integer ranging from 1 to 34, $X^-$ denotes an anion such as a halide, A denotes a dihalide radical or preferably represents —$CH_2$—$CH_2$—O—$CH_2$—$CH_2$—.

Such compounds are described in particular in patent application EP-122 324.

Among these products, mention may be made, for example, of "Mirapol® A 15", "Mirapol® AD1", "Mirapol® AZ1" and "Mirapol® 175" by the company Miranol.

(12) Quaternary polymers of vinylpyrrolidone and of vinylimidazole, such as, for example, the products sold under the names Luviquat® FC 905, FC 550 and FC 370 by the company BASF.

(13) Polyamines such as Polyquart® H sold by Cognis, which is given under the reference name "Polyethylene glycol (15) tallow polyamine" in the CTFA dictionary.

(14) Crosslinked methacryloyloxy($C_1$–$C_4$)alkyltri($C_1$–$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethyl-ammonium chloride copolymer (20/80 by weight) in the form of a dispersion containing 50% by weight of the copolymer in mineral oil can be used more particularly. This dispersion is sold under the name "Salcare® SC 92" by the company Ciba Geigy. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Ciba Geigy.

Other cationic polymers that can be used in the context of the invention are cationic proteins or cationic protein hydrolysates, polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers that may be used in the context of the present invention, it is preferred to use quaternary cellulose ether derivatives such as the products sold under the name "JR 400" by the company Amerchol, cationic cyclopolymers, in particular the dimethyldiallylammonium chloride homopolymers or copolymers sold under the names "Merquat® 100", "Merquat® 550" and "Merquat® S" by the company Nalco, cationic polysaccharides such as guar gums modified with a 2,3-epoxypropyltrimethylammonium salt, quaternary polymers of vinylpyrrolidone and of vinylimadazole, and mixtures thereof.

During a step c), which may or may not be performed immediately after step b), or alternatively after step a), the keratin fibres are treated with a washing composition (B). Preferably, when step c) takes place after step b), this treatment takes place at least 12 hours after the application of the dye composition and preferably at least 24 hours after.

The washing composition (B) comprises as surfactant at least one nonionic surfactant chosen from alkylpolyglucosides and monoglycerolated or polyglycerolated surfactants, and mixtures thereof.

As regards the alkylpolyglucosides, these compounds are well known and may be represented more particularly by the following general formula:

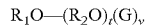

in which $R_1$ represents a linear or branched alkyl and/or alkenyl radical containing from about 8 to 24 carbon atoms, an alkylphenyl radical in which the linear or branched alkyl radical contains from 8 to 24 carbon atoms, $R_2$ represents an alkylene radical containing from about 2 to 4 carbon atoms, G represents a sugar unit containing 5 or 6 carbon atoms, t denotes a value ranging from 0 to 10 and preferably from 0 to 4, and v denotes a value ranging from 1 to 15.

Alkylpolyglycosides that are preferred according to the present invention are compounds of formula (II) in which $R_1$ more particularly denotes a saturated or unsaturated, linear or branched alkyl radical containing from 8 to 18 carbon atoms, t denotes a value ranging from 0 to 3 and even more particularly equal to 0, and G may denote glucose, fructose or galactose, preferably glucose. The degree of polymerization, i.e. the value of v in formula (II), may range from 1 to 15 and preferably from 1 to 4. The mean degree of polymerization is more particularly between 1 and 2.

The glycoside bonds between the sugar units are of 1–6 or 1–4 type and preferably of 1–4 type.

Compounds of formula (II) are especially represented by the products sold by the company Cognis under the names Plantaren® (600 CS/U, 1200 and 2000) or Plantacare® (818, 1200 and 2000). It is also possible to use the products sold by the company SEPPIC under the names Triton CG 110 (or Oramix CG 110) and Triton CG 312 (or Oramix® NS 10), the products sold by the company BASF under the name Lutensol GD 70 or the products sold by the company Chem Y under the name AG10 LK.

It is also possible to use, for example, C8/C16 alkyl polyglucoside-1,4 as an aqueous 53% solution sold by Cognis under the reference Plantacare® 818 UP.

As regards the monoglycerolated or polyglycerolated surfactants, they preferably comprise on average from 1 to 30 glycerol groups, more particularly from 1 to 10 and in particular from 1.5 to 5 glycerol groups.

The monoglycerolated or polyglycerolated surfactants are preferably chosen from the following compounds of formulae: $RO[CH_2CH(CH_2OH)O]_mH$, $RO[CH_2CH(OH)CH_2O]_mH$ or $RO[CH(CH_2OH)CH_2O]_mH$; in which R represents a saturated or unsaturated, linear or branched hydrocarbon-based radical containing from 8 to 40 carbon atoms and preferably from 10 to 30 carbon atoms; m is an integer between 1 and 30, preferably between 1 and 10 and more particularly from 1.5 to 6.

R may optionally comprise hetero atoms, for instance oxygen and nitrogen. In particular, R may optionally comprise one or more hydroxyl and/or ether and/or amide groups.

R preferably denotes optionally monohydroxylated or polyhydroxylated $C_{10}$–$C_{20}$ alkyl and/or alkenyl radicals.

The polyglycerolated (3.5 mol) hydroxylauryl ether sold under the name Chimexane® NF from Chimex may be used, for example.

In accordance with one particular embodiment of the invention, the total content of nonionic surfactant is between 4% and 50% by weight relative to the weight of the washing composition (B), and preferably between 6% and 30% by weight relative to the weight of the washing composition (B).

The washing composition (B) may also comprise additional surfactants chosen from anionic, amphoteric and zwitterionic surfactants, and mixtures thereof.

Everything that has been stated previously regarding the nature of the amphoteric, zwitterionic and mild anionic surfactants remains valid and will not be repeated.

The anionic surfactants may be mild anionic surfactants such as those described above, but also strong anionic surfactants such as alkyl ether sulfates or alkyl sulfates.

If additional surfactants are present, then the total content of detergent surfactant(s) of this type is preferably between 4% and 50% by weight relative to the total content of detergent surfactants present in the washing composition (B), and more particularly between 6% and 30% by weight relative to the same reference.

The total content of amphoteric, zwitterionic and anionic surfactants is generally preferably between 1% and 20% by weight relative to the weight of the washing composition (B), and more preferably between 1% and 15% by weight relative to the weight of the washing composition (B).

Preferably, the washing composition (B) does not contain any strong anionic detergent surfactant of alkyl sulfate or alkyl ether sulfate type. Moreover, if it does contain any, its content is such that the weight ratio: anionic detergent surfactant of alkyl sulfate or alkyl ether sulfate type/sum of the amphoteric, zwitterionic, mild anionic and/or nonionic surfactants is less than or equal to 0.6 and more particularly less than or equal to 0.2.

According to one preferred embodiment of the invention, the washing composition (B) comprises at least one conditioning agent, which is preferably cationic.

Reference may be made to the description of these compounds given in the context of the description of the second washing composition (B).

According to this preferred embodiment, the content of conditioning agent in the second washing composition is between 0.01% and 20% by weight relative to the weight of the first washing composition.

According to another preferred embodiment of the invention, the washing composition (B) comprises at least one thickener identical to those described for the washing composition (A), although the thickeners in A and B may be different.

When a thickener is used, its content in the second washing composition (B) is preferably between 0.01% and 20% by weight relative to the weight of the washing composition (B).

Finally, the washing composition (B) may comprise additives, and especially those mentioned in the context of the washing composition (A), in the contents indicated previously.

Once the washing operation(s) has (have) been performed, the fibres are dried or are left to dry.

In accordance with a first variant of the invention, step c) of the process, i.e. the washing using the washing composition (B), is performed directly after step a) of the process (dyeing step).

Thus, the keratin fibres are rinsed to remove the excess dye composition and are then washed one or more times with the washing composition (B), usually with intermediate rinsing.

It should be noted that step c) may be performed several times, at the frequency conventionally used between two shampoo washes (i.e., for example with time intervals of between 12 hours and two weeks).

According to another possibility, the washing step c) with the washing composition (B) is performed with a delay relative to a prior step b) and/or relative to a prior step c).

In this case, the process consists in successively performing the steps a) and b) or a) and c) and then, after the second step (either step b) or step c)), in drying the fibres or leaving them to dry. Step c) is then performed after a longer or shorter time, preferably at least 12 hours after the application, or alternatively preferably at least 24 hours after the application, of the dye composition.

Another subject of the present invention is a kit for performing the invention processes, first comprising a dye composition and optionally a composition comprising at least one oxidizing agent; and then optionally at least one washing composition (A) and finally at least one washing composition (B). In one embodiment the dye composition is optional.

Everything that has been detailed previously regarding the nature of the constituent components of the various compositions and the proportions thereof remains valid and will not be repeated in this part of the description.

Another subject of the invention is the use of a washing composition comprising, as surfactant, at least one nonionic surfactant chosen from alkylpolyglycosides and monoglycerolated or polyglycerolated surfactants, or mixtures thereof, for protecting the coloration and/or for limiting the bleeding of the coloration of keratin fibres, the coloration being obtained by means of a dye composition comprising at least one cationic direct dye.

Preferably, the total content of nonionic surfactants is between 4% and 50% by weight relative to the weight of the washing composition, and more preferably between 6% and 30% by weight relative to the weight of the washing composition.

In addition, this washing composition may comprise at least one detergent surfactant chosen from amphoteric, zwitterionic and additional anionic surfactants preferably chosen from alkyl ether sulfates and/or alkyl sulfates.

Preferably, the washing composition contains no anionic detergent surfactant of alkyl sulfate or alkyl ether sulfate type. Moreover, if it does contain any, its content is preferably such that the weight ratio: anionic detergent surfactant of alkyl sulfate or alkyl ether sulfate type/sum of the nonionic surfactants is less than or equal to 0.6 and more particularly less than or equal to 0.2.

It should be noted that the washing composition may comprise at least one conditioning agent, which is preferably cationic.

Moreover, when the composition comprises such an agent, its content is preferably between 0.01% and 20% by weight relative to the weight of the washing composition.

It is recalled that reference may be made to the description as regards the more specific nature of the ingredients included in this washing composition.

Concrete but non-limiting examples of the invention will now be presented.

EXAMPLES

Dyeing steps:
The dye compositions detailed in Table 1 below were prepared from two types of cationic direct dye:
cationic dye whose charge is borne by a heterocycle: Basic Red 51 (Vibracolor Ruby Red—Ciba Geigy)
cationic dye not containing a heterocycle: Basic Red 76 (Arianor Madder Red 306003—LCW).

At the time of use, each of the above compositions was mixed weight for weight with aqueous hydrogen peroxide solution (L'Oréal professional 20-volumes 6% aqueous hydrogen peroxide solution).

TABLE 1

|  | Coloration 1 | Coloration 2 |
|---|---|---|
| Oramix ® CG 110 decyl glucoside as an aqueous 60% solution (SEPPIC) | 5.4 g | 5.4 g |
| Denatured 96 degree ethyl alcohol | 18 g | 18 g |
| Benzyl alcohol | 1.8 g | 1.8 g |
| Polyethylene glycol (8 OE) | 2.7 g | 2.7 g |
| Pentasodium pentetate at 40% in water | 1.08 g | 1.08 g |

TABLE 1-continued

|  | Coloration 1 | Coloration 2 |
|---|---|---|
| Basic Red 51 | 0.25 g | — |
| Basic Red 76 | — | 0.25 g |
| 20.5% aqueous ammonia | 13 g | 13 g |
| Demineralized water | qs 100 | qs 100 |

The mixture was then applied to moderately bleached pigmented locks of hair, at a rate of 10 g of dye mixture/gram of lock. The leave-in time was 15 minutes on each side of the lock.

The dyeing was then stopped by rinsing with water, followed by washing with a commercial shampoo containing sodium laureth sulfate as anionic surfactant (DOP camomile shampoo). The locks were then dried for 30 minutes at 60° C. under a hood.

Washing Steps 48 hours after performing the colorations described above, two types of shampoo were evaluated:

The compositions are detailed in Table 2:

TABLE 2

|  | Shampoo 1 | Shampoo 2 |
|---|---|---|
| Texapon ® N702 sodium laureth sulfate at 70% in water (Cognis) | — | 21.43 g |
| Cocoglucoside at 53% in water (Plantacare ® 818 UP - Cognis) | 28.30 g | — |
| Citric acid | qs pH = 7 | qs pH = 7 |
| Water | qs 100 | qs 100 |

The application conditions were as follows:

after wetting the hair with water (running wet fingers through three times), each lock was drained between two fingers and an amount of 0.4 g of shampoo/gram of the hair was applied along the lock of hair (uniformly from the root to the end).

A lather was then produced by gently massaging the lock along its length between two fingers for 15 seconds from top to bottom (without making any knots). The lock was then wound round the fingers and placed in a plastic dish.

It was then left to stand for a measured time of 5 minutes for each application, and the duration of the lather was observed. The level of duration was quantified (0: absence of lather after 5 minutes, 5: good duration of lather).

The locks were then rinsed, drained between two fingers, combed and dried under a hood for 30 minutes at 60° C.

Results: The Results are Collated in Table 3 Below:

1. Duration of the lather:

After 5 minutes, a marked improvement in the duration of the lather was noted with the alkylpolyglucoside relative to sodium laureth sulfate.

Moreover, it was observed that with the alkylpolyglucoside, the lather remains markedly more abundant on the coloration with Basic Red 51.

TABLE 3

|  | Shampoo 1 (containing cocoglucoside) | | Shampoo 2 (containing sodium laureth sulfate) | |
|---|---|---|---|---|
| Shampoos applied Coloration | Coloration 1 (Basic Red 51) | Coloration 2 (Basic Red 76) | Coloration 1 (Basic Red 51) | Coloration 2 (Basic Red 76) |
| Lather duration t = 1sh-5 min | 5 | 3 | 0 | 0 |

Moreover, each shampoo was applied ten times and evaluations were made, after each application, firstly of the bleeding of the colour into the rinsing water and into the lather, and also of the fastness of the coloration, which was observed visually 48 hours after drying the locks.

It was found that the bleeding of the colour into the water and into the lather was smaller in the case of the present invention, which was reflected by less staining of towels, pillowcases, etc.

It was also observed that the fastness of the coloration applied according to the process of the invention was greater.

The above written description of the invention provides a manner and process of making and using it such that any person skilled in this art is enabled to make and use the same, this enablement being provided in particular for the subject matter of the appended claims, which make up a part of the original description and including a process for treating human keratin fibres, in which the following steps are performed:
a) a step of dyeing the fibres is performed using a ready-to-use composition based on a dye composition comprising at least one cationic direct dye containing at least one heterocyclic group;
b) optionally, the fibres are washed with a washing composition (A) comprising at least one anionic detergent surfactant chosen from alkyl ether sulfates and/or alkyl sulfates, and the fibres are rinsed and optionally dried or left to dry;
c) the fibres are washed with a washing composition (B) comprising at least one nonionic surfactant chosen from alkylpolyglucosides and monoglycerolated or polyglycerolated surfactants, and mixtures thereof, and the fibres are then rinsed and dried or left to dry.

Preferred embodiments of the invention similarly fully described and enabled include a process for treating human keratin fibres, comprising:
a) optionally washing fibres that have been dyed with a dye composition comprising at least one cationic direct dye, said cationic direct dye comprising at least one heterocyclic group, with a washing composition (A) comprising at least one anionic detergent surfactant selected from the group consisting of alkyl ether sulfates, alkyl sulfates, and mixtures thereof, rinsing said fibres, and optionally drying said fibres or leaving said fibres to dry;
b) washing said fibres that have been dyed with a dye composition comprising at least one cationic direct dye, said cationic direct dye comprising at least one heterocyclic group, with a washing composition (B) comprising at least one nonionic surfactant selected from the group consisting of alkylpolyglucosides, monoglycerolated surfactants, polyglycerolated surfactants, and mixtures thereof, and drying said fibres or leaving said fibres to dry.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A process for treating human keratin fibres, comprising:
a) dyeing the keratin fibers with a dye composition comprising at least one cationic direct dye, said cationic direct dye comprising at least one heterocyclic group;
b) optionally washing the dyed keratin fibres with a washing composition (A) comprising at least one anionic detergent surfactant selected from the group consisting of alkyl ether sulfates, alkyl sulfates, and mixtures thereof, rinsing said fibres, and optionally drying said fibres or leaving said fibres to dry;
c) washing said fibres that have been dyed with a dye composition comprising at least one cationic direct dye, said cationic direct dye comprising at least one heterocyclic group, with a washing composition (B) comprising at least one nonionic surfactant selected from the group consisting of alkylpolyglucosides, monoglycerolated surfactants, polyglycerolated surfactants, and mixtures thereof, rinsing the fibres washed with washing composition (B), and drying said rinsed fibres or leaving said rinsed fibres to dry.

2. A process as claimed in claim 1, wherein the dye composition comprises at least one cationic direct dye comprising a heterocycle bearing at least one cationic charge.

3. A process as claimed in claim 1, wherein the total content of cationic direct dyes represents 0.0001% to 20% by weight relative to the weight of the dye composition.

4. A process as claimed in claim 1, wherein the dye composition further comprises at least one oxidation base and optionally at least one coupler.

5. A process as claimed in claim 4, wherein the total content of oxidation base is between 0.0005% and 12% by weight relative to the weight of the dye composition.

6. A process as claimed in claim 4, wherein the dye composition further comprises at least one coupler and the total content of coupler represents from 0.0001% to 10% by weight relative to the weight of the dye composition.

7. A process as claimed in claim 1, wherein the dye composition is a ready-to use composition that further comprises at least one oxidizing agent.

8. A process as claimed in claim 7, wherein the oxidizing agent is selected from the group consisting of hydrogen peroxide, urea peroxide, alkali metal bromates or ferricyanides, persalts, redox enzymes, and mixtures thereof, where appropriate in the presence of the respective donor thereof.

9. A process as claimed in claim 1, wherein the dye composition is a ready-to-use composition obtained by mixing, before application to the fibres, a dye composition with a composition comprising at least one oxidizing agent.

10. A process as claimed in claim 1, comprising step b), and wherein the content of anionic detergent surfactant in the washing composition (A) is between 4% and 50% by weight relative to the weight of washing composition (A).

11. A process as claimed in claim 1, wherein the washing composition (B) comprises at least one alkylpolyglucoside represented by the following general formula:

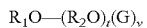

in which $R_1$ represents a linear or branched alkyl and/or alkenyl radical containing from 8 to 24 carbon atoms, an alkylphenyl radical in which the linear or branched alkyl radical contains from 8 to 24 carbon atoms, $R_2$ represents an alkylene radical containing from 2 to 4 carbon atoms, G represents a reduced sugar containing 5 or 6 carbon atoms, t denotes a value ranging from 0 to 10, and v denotes a value ranging from 1 to 15.

12. A process as claimed in claim 1, wherein the washing composition (B) comprises at least one monoglycerolated or polyglycerolated surfactant of the following formulae: $RO[CH_2CH(CH_2OH)O]_mH$, $RO[CH_2CH(OH)CH_2O]_mH$ or $RO[CH(CH_2OH)CH_2O]_mH$; in which R represents a saturated or unsaturated, linear or branched hydrocarbon-based radical containing from 8 to 40 carbon atoms; and m is an integer between 1 and 30.

13. A process as claimed in claim 12, wherein R denotes optionally monohydroxylated or polyhydroxylated $C_{10}$–$C_{20}$ alkyl and/or alkenyl radicals.

14. A process as claimed in claim 1, wherein the total content of nonionic surfactant in washing composition (B) is between 4% and 50% by weight relative to the weight of the washing composition (B).

15. A process as claimed in claim 1, wherein washing composition (B) further comprises at least one surfactant selected from the group consisting of amphoteric, zwitterionic and anionic surfactants, and mixtures thereof.

16. A process as claimed in claim 1, wherein washing composition (B) further comprises at least one amphoteric and/or zwitterionic surfactant selected from the group consisting of aliphatic secondary or tertiary amine derivatives, in which the aliphatic radical is a linear or branched chain having from 8 to 18 carbon atoms and at least one water-solubilizing anionic group; $(C_8$–$C_{20})$alkylbetaines, sulfobetaines, $(C_8$–$C_{20})$alkylamido$(C_1$–$C_6)$alkylbetaines and $(C_8$–$C_{20})$alkylamido$(C_1$–$C_6)$alkylsulfobetaines, and mixtures thereof.

17. A process according to claim 14, wherein the washing composition (B) further comprises at least one anionic surfactant selected from the group consisting of:
polyoxyalkylenated alkyl ether carboxylic acids;
polyoxyalkylenated alkylaryl ether carboxylic acids;
polyoxyalkylenated alkylamido ether carboxylic acids;
alkyl-D-galactosiduronic acids;
acylsarcosinates and acylglutamates;
alkylpolyglycoside carboxylic esters;
fatty acid salts.

18. A process according to claim 15, wherein the total content of amphoteric, zwitterionic and anionic surfactants is between 1% and 20% by weight relative to the weight of the washing composition (B).

19. A process according to claim 1, wherein washing composition (A) and/or washing composition (B) further comprises at least one conditioning agent.

20. A process as claimed in claim 19, wherein the conditioning agent is a cationic polymer or a silicone.

21. A process as claimed in claim 19, wherein the conditioning agent is an amino silicone.

22. A process according to claim 19, wherein the content of conditioning agent in the washing composition(s) (A) and/or (B) is between 0.01% and 20% by weight relative to the weight, respectively, of the washing composition(s) (A) and/or (B).

23. A process according to claim 1, wherein washing composition(s) (A) and/or (B) further comprise(s) at least one thickener.

24. A process as claimed in claim 23, wherein the content of thickener in the washing composition(s) (A) and/or (B) is between 0.01% and 20% by weight relative to the weight of the washing composition (A) or (B), respectively.

25. A process according to claim 1, wherein washing composition (B) is packaged in an aerosol device.

26. A process as claimed in claim 25, wherein the device further comprises a propellant.

27. A process as claimed in claim 26, wherein the propellant comprises a compressed or liquefied gas, or a mixture thereof.

28. A process according to claim 1, not comprising step b).

29. A process as claimed in claim 1, wherein the keratin fibres are rinsed to remove any excess dye composition, and the fibres are then washed one or more times with the washing composition (B), usually with intermediate rinsing.

30. A process according to claim 1, wherein washing composition (B) is applied at least 12 hours after the fibres have been dyed.

31. A process according to claim 1, wherein step c) is performed several times, at the frequency conventionally used between two shampoo washes.

32. A process as claimed in claim 31, wherein the frequency is between 12 hours and 2 weeks.

33. Process according to claim 1, wherein step c) is performed in a delayed manner relative to a prior step b).

34. A process as claimed in claim 1,
wherein steps a) and c) are performed successively and wherein the process further comprises drying the fibers or leaving them to dry prior to performing step c).

35. A process as claimed in claim 34, wherein step c) is performed at least 12 hours after the application of the dye composition.

36. A kit comprising a dye composition comprising at least one cationic direct dye comprising at least one heterocyclic group and optionally a composition comprising at least one oxidizing agent; optionally at least one washing composition (A) comprising at least one anionic detergent surfactant selected from the group consisting of alkyl ether sulfates, alkyl sulfates, and mixtures thereof, and at least one washing composition (B) comprising at least one nonionic surfactant selected from the group consisting of alkylpolyglucosides, monoglycerolated surfactants, polyglycerolated surfactants, and mixtures thereof.

37. A process for limiting the bleeding of the coloration and/or for improving the protection of the coloration of keratin fibres, in relation with the prior use of a dye composition comprising at least one cationic direct dye comprising at least one heterocyclic group, comprising washing said fibres with a washing composition comprising at least one nonionic surfactant selected from the group consisting of alkylpolyglycosides, monoglycerolated surfactants, polyglycerolated surfactants, and mixtures thereof.

38. A process according to claim 37, wherein the total content of nonionic surfactant is between 4% and 50% by weight relative to the weight of the washing composition.

39. The process according to claim 37, wherein the washing composition further comprises at least one conditioning agent.

40. The process according to claim 39, wherein the conditioning agent is a cationic polymer and/or an amino silicone.

41. The process according to claim 39, wherein the content of conditioning agent is between 0.01% and 20% by weight relative to the weight of the washing composition.

* * * * *